United States Patent [19]

Moyne et al.

[11] Patent Number: 4,588,532

[45] Date of Patent: May 13, 1986

[54] PREPARATION OF PARA-ACYLOXYBENZENE SULFONATES

[75] Inventors: José Moyne, Caluire; Camille Disdier, Lyons, both of France

[73] Assignee: Rhone-Poulenc Chimie de Base, Courbevoie, France

[21] Appl. No.: 702,733

[22] Filed: Feb. 19, 1985

[30] Foreign Application Priority Data

Feb. 17, 1984 [FR] France .................... 84 02398

[51] Int. Cl.$^4$ .................... C07C 143/46; C07C 143/38
[52] U.S. Cl. .................... 260/402; 560/142
[58] Field of Search .................... 260/402; 560/142

[56] References Cited

U.S. PATENT DOCUMENTS

| 628,503 | 7/1899 | Twitchell | 260/402 |
|---|---|---|---|
| 1,642,595 | 9/1927 | Petroff et al. | 260/402 |
| 3,383,396 | 5/1968 | Cahn et al. | 260/402 |
| 3,394,155 | 7/1968 | Cahn et al. | 260/402 |
| 3,636,016 | 1/1972 | McGuire | 260/402 |
| 3,775,445 | 11/1973 | McGuire et al. | 260/402 |

FOREIGN PATENT DOCUMENTS

| 2299321 | 1/1976 | France | 260/402 |
|---|---|---|---|
| 363770 | 12/1931 | United Kingdom | 260/402 |
| 852110 | 10/1956 | United Kingdom | 260/402 |

Primary Examiner—Bernard Helfin
Attorney, Agent, or Firm—Burns, Doane, Swecker & Mathis

[57] ABSTRACT p-Acyloxybenzene sulfonates, well suited for detergency applications, are facilely and rapidly prepared by acylating an alkali or alkaline earth metal, or ammonium p-phenol sulfonate, with an anhydride of a straight or branched chain carboxylic acid having from 7 to 12 carbon atoms, in a polar aprotic solvent and in the presence of a catalytically effective amount of an organic sulfonic acid.

23 Claims, No Drawings

PREPARATION OF PARA-ACYLOXYBENZENE SULFONATES

CROSS-REFERENCE TO RELATED APPLICATION

Our copending application, Ser. No. 702,732 filed concurrently herewith and assigned to the assignee hereof.

BACKGROUND OF THE INVENTION

1. Field of the Invention

The present invention relates to the preparation of para-acyloxybenzene sulfonates, and, more especially, to the preparation of para-acyloxybenzene sulfonates by acid catalysis, and wherein the acyloxy moiety of such sulfonates contains from 7 to 12 carbon atoms.

2. Description of the Prior Art

It is known to this art, from French Pat. No. 2,164,619, Example 1, to prepare the title compounds from an aliphatic acid chloride and potassium phenol sulfonate by direct condensation in an anhydrous reaction medium. The speed of condensation between the acid chloride and the phenol sulfonate is extremely slow (20 hours at 150° C.) and the product formed is very difficult to isolate. A large amount of HCl also forms in the process and is not always easy to eliminate.

It is also known [see Pueschel, *Tenside*, 7 (5), pp. 249–54 (1970)] to prepare these compounds by a method which differs slightly from that of French Pat. No. 2,164,619, but in the presence of an acid acceptor to avoid the elimination of gaseous hydrochloric acid. The product formed is neutralized by sodium carbonate, but as a result it is very difficult to separate the product obtained from the sodium chloride formed during neutralization.

The slowness of the reaction in which the acid chloride is condensed with the phenol sulfonate has prompted those skilled in this art to raise the reaction temperature considerably, but strongly colored products are then formed. Since such products are in fact principally used in detergency, however, it is necessary to produce perfectly white materials in order to meet commercial requirements.

It too is known, from French Pat. No. 2,299,321, to prepare para-acyloxybenzene sulfonates by condensing a powdered phenol sulfonate with acetic anhydride in vapor state; the reaction can be carried out dry, for acetic anhydride has a boiling point of 140° C., but it is not possible to proceed in this fashion as a means for condensing, e.g., nonanoic anhydride, with phenol sulfonate, since nonanoic anhydride has a boiling point of 260° C.

Nonetheless, it was hitherto unknown to condense an acid anhydride with a phenol sulfonate in a liquid reaction medium.

SUMMARY OF THE INVENTION

Accordingly, a major object of the present invention is the provision of an improved process for the preparation of para-acyloxybenzene sulfonates which is both quick and easy, is carried out in a liquid reaction medium, gives rise to the production of an easily separated reaction product in completely colorless state, and which otherwise avoids those disadvantages and drawbacks to date characterizing the state of this art.

Briefly, the present invention features the preparation of para-acyloxybenzene sulfonates having the general formula (I):

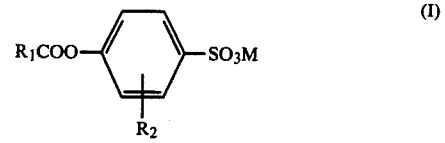

wherein $R_1$ is a straight or branched chain aliphatic radical containing from 6 to 11 carbon atoms, $R_2$ is hydrogen, halogen, an alkyl radical having from 1 to 4 carbon atoms or the radical $-SO_3M$, and M is an alkali or alkaline earth metal or an ammonium group, by acylating an alkali or alkaline earth metal or ammonium phenol sulfonate with an anhydride of a straight or branched chain carboxylic acid containing from 7 to 12 carbon atoms, in a polar aprotic solvent and in the presence of a catalytically effective amount of an organic sulfonic acid.

DETAILED DESCRIPTION OF THE INVENTION

More particularly according to the present invention, exemplary reactant aliphatic anhydrides include heptanoic, octanoic, caprylic, nonanoic, pelargonic, decanoic, capric, dodecanoic, and lauric anhydrides. Preferably employed are the anhydrides of those carboxylic acids containing 9 carbon atoms. More preferred are pelargonic anhydride and 3,5,5-trimethylhexanoic anhydride, since these materials are readily commercially available.

The reactant acid anhydrides may be prepared in known manner by any one of a number of processes. In a first embodiment, described in *Collective Organic Syntheses*, 3, p. 28, John Wiley (1955), the acid chloride is contacted with the acid and a tertiary base, which will neutralize the acid formed. This gives the required anhydride and a hydrochloride with a tertiary base. In a second embodiment, described in *Journal of Chemical Society*, p. 755 (1964), the acid chloride and the sodium salt of the acid are contacted in water. This gives the required anhydride and sodium chloride. Since the reaction is carried out in water, the anhyd.idre formed need not be easily hydrolyzable.

In a third embodiment, acetic anhydride is reacted with the acid according to the following mechanism:

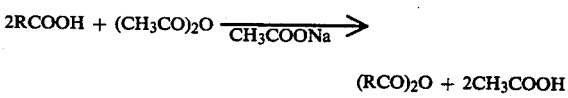

$$(RCO)_2O + 2CH_3COOH$$

It is preferred to carry out this particular reaction in the presence of an excess of acetic anhydride, which is distilled upon completion of the reaction.

Consistent herewith, it is preferred to use an acid anhydride which has been obtained in accordance with the aforesaid third embodiment.

As regards the various phenol sulfonates, it is preferred to use those in which $R_2$ is hydrogen, and more preferably the phenol sulfonate of sodium or potassium, since these compounds are the most readily commercially available.

Representative of the polar aprotic solvents intended, the following are exemplary:

(i) dimethylformamide;
(ii) N-methylpyrrolidone;
(iii) dimethylacetamide;
(iv) dimethylsulfoxide; and
(v) sulfolane The solvent should nevertheless be odorless, for it is commercially impossible to incorporate a malodorous substance in a detergent. The boiling point of the solvent must not be too high, and its manufacturing cost must be low enough not to impose an unnecessary increase in the cost of the product to be obtained. From among all of the solvents intended, dimethylformamide is the preferred as it best conforms to the aforesaid conditions.

The organic sulfonic acid which is used as the catalyst for the condensation reaction has the following general formula (II):

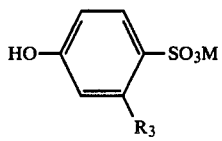

(II)

in which $R_3$ is hydrogen, an alkyl radical containing from 1 to 12 carbon atoms, haloalkyl, phenyl, alkylphenyl, nitro, halogen and $SO_3M$, wherein M is as defined above.

Exemplary of such organic sulfonic acids having the general formula (II), representative are para-toluenesulfonic acid, benzenesulfonic acid and nitrobenzenesulfonic acid.

The acid selected must be a strong acid which, however, is non-oxidizing, in order to avoid any coloration of the final product. Preferably, para-toluenesulfonic acid is used.

To obtain a proper reaction speed it is preferable to use a molar excess of the anhydride relative to the phenol sulfonate. For a proper economic yield it is still more preferable to add an excess of anhydride of at least 0.3 mole relative to the stoichiometry of the reaction.

The molar ratio of solvent to phenol sulfonate preferably ranges from 5 to 50. A larger amount is not outside of the scope of the invention, but such amounts will have to be adapted to the economics of the process. The molar ratio more preferably ranges from 5 to 10 and still more preferably from 7 to 10.

The molar ratio of the sulfonic acid (II) to the phenol sulfonate preferably is in excess of about 0.01 and more preferably is about 0.02.

The reaction temperature influences the speed of reaction; accordingly, a temperature in excess of 100° C. is advantageous. Above a temperature of 125° C. secondary reactions occur between the anhydride and the solvent, particularly when using dimethylformamide, with the formation of amides which considerably reduce yields. The preferred reaction temperature thus ranges from 110° to 120° C.

The reaction is typically carried out at atmospheric pressure, although a higher pressure is also not deleterious to the process of the invention.

The final products according to the invention may facilely be extracted from the reaction medium by washing same with acetone, at a temperature of 90° C. or above, and preferably from 90° to 100° C., by adding approximately the same weight of acetone as that of solvent introduced.

The title para-acyloxybenzene sulfonates are used in detergency application, notably as surfactants. Especially representative formula (I) compounds are: sodium p-3,5,5-trimethylhexanoyloxybenzene sulfonate, sodium p-octanoylbenzene sulfonate and sodium p-dodecanoyloxybenzene sulfonate.

In order to further illustrate the present invention and the advantages thereof, the following specific examples are given, it being understood that same are intended only as illustrative and in nowise limitative.

EXAMPLE 1

Preparation of sodium p-3,5,5-trimethylhexanoyloxybenzene sulfonate

[1] Preparation of 3,5,5-trimethylhexanoic anhydride (TMH anhydride)

Into a 1500 liter reaction vessel, upon which a distillation column was surmounted, 632 kg of trimethylhexanoic acid (3.99 Kmoles), 408 kg of acetic anhydride (3.99 Kmoles) and 0.1 kg of sodium acetate were introduced. The catalyst was selected because it only slightly discolored the TMH anhydride. The reaction mixture was raised to a temperature of 90° C. under a vacuum of 12,000 Pa to permit distillation of the acetic acid formed; the vacuum was then adjusted such that the temperature of the distillation vessel increased. The reaction was completed after 3 hours at:

T°=110° C.; Pressure=660 Pa.

The reaction mixture was raised to a temperature of 160° C. (under 1,300 Pa) to remove the excess acetic anhydride.

The product 3,5,5-trimethylhexanoic anhydride, which was very slightly colored, was not distilled but was used as such:

Weight=596 kg
Yield=100%

[2] Condensation of TMH anhydride with sodium p-phenol sulfonate

Introduced into a 2 cubic meter reaction vessel, with a small column ascending thereabove, were 800 kg of dimethylformamide, 301 kg of sodium p-phenol sulfonate which was dried at 160° C. under 2,600 Pa ($H_2O<0.5\%$) and 6 kg of p-toluenesulfonic acid.

The reaction mixture was raised to a temperature of 115° C. and 596 kg of TMH anhydride (30% excess) were introduced therein over one half to three quarters of an hour.

The temperature was maintained for 6 hours without exceeding 120° C. in order to avoid the DMF decomposition reaction.

800 kg of acetone were introduced at a temperature of from 90° to 100° C. in order to remove the ester which was dissolved in the DMF.

Cooling to ambient temperature was next carried out.

The ester was filtered, under pressure, through a filter having a surface area of 6 m².

The filtered product was washed with acetone and dried at 150° C. under 2,600 Pa.

Weight=476 kg
Yield=92%.

The solutions were distilled and recycled.

EXAMPLE 2

Preparation of sodium p-octanoyloxybenzene sulfonate

Octanoic anhydride was produced under the same conditions as in the foregoing Example.

The following materials were introduced into a 2 cubic reaction vessel: 550 kg of DMF, 6 kg of p-toluenesulfonic acid, 301 kg of dehydrated sodium p-phenol sulfonate and 300 kg of octanoic anhydride.

The reaction mixture was raised to 115° C. and 342 kg of octanoic anhydride (40% excess) were added over half an hour.

The reaction was complete after 5 hours.

550 kg of acetone were added at a temperature of 90° to 100° C. Cooling to ambient temperature was next carried out.

At ambient temperature, the product was filtered.

After washing with acetone and drying at 150° C. under 2,600 Pa, the following were recovered:

Weight=493 kg of sodium p-octanoyloxybenzene sulfonate;
Yield=95%.

EXAMPLE 3

The reaction conditions of this Example were the same as those set forth in Example 1, except that the para-toluenesulfonic acid was replaced by meta-nitrobenzenesulfonic acid (2 kg).

After reaction and after the removal operation, the product obtained was 493 kg of sodium p-3,5,5-trimethylhexanoyloxybenzene sulfonate, in a yield of 95%.

EXAMPLE 4

Preparation of sodium p-3,5,5-trimethylhexanoyloxybenzene sulfonate

The reaction conditions of this Example were the same as those set forth in Example 1, except that the para-toluenesulfonic acid was replaced by benzenesulfonic acid (2 kg).

After the reaction and the removal operation, 470 kg of sodium p-3,5,5-trimethylhexanoyloxybenzene sulfonate were obtained, in a yield of 90%.

EXAMPLE 5

Preparation of sodium dodecanoyloxybenzene sulfonate

Dodecanoic anhydride was produced under the same conditions as set forth in Example 1.

The following materials were introduced into a 2 cubic meter reaction vessel: 600 kg of DMF, 4 kg of para-toluenesulfonic acid, 200 kg of dehydrated sodium para-phenolsulfonate and 500 kg of dodecanoic anhydride.

The reaction medium was maintained at 115° C. for 5 hours.

800 kg of acetone were added at a temperature of from 90° to 100° C., followed by cooling to ambient temperature and filtration.

The product obtained was 265 kg of sodium p-dodecanoyloxybenzene sulfonate, in a yield of 70%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a para-acyloxybenzene sulfonate having the general formula (I):

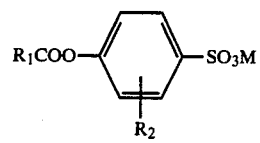

wherein $R_1$ is a straight or branched chain aliphatic radical having from 6 to 11 carbon atoms, $R_2$ is hydrogen, halogen, an alkyl radical having from 1 to 4 carbon atoms, or the radical $-SO_3M$, and M is an alkali or alkaline earth metal, or ammonium, which process comprises acylating an alkali or alkaline earth metal, or ammonium p-phenol sulfonate, with an anhydride of a straight or branched chain carboxylic acid having from 7 to 12 carbon atoms, in a polar aprotic solvent and in the presence of a catalytically effective amount of an organic sulfonic acid.

2. The process as defined by claim 1, said p-phenol sulfonate comprising sodium or potassium p-phenol sulfonate.

3. The process as defined by claim 1, said acid anhydride comprising an anhydride of a carboxylic acid having 9 carbon atoms.

4. The process as defined by claim 1, said polar aprotic solvent comprising dimethylformamide, dimethylacetamide, N-methylpyrrolidone, dimethylsulfoxide or sulfolane.

5. The process as defined by claim 4, said polar aprotic solvent comprising dimethylformamide.

6. The process as defined by claim 1, said organic sulfonic acid comprising para-toluenesulfonic acid.

7. The process as defined by claim 1, wherein the molar ratio of acid anhydride to p-phenol sulfonate is at least 1.3.

8. The process as defined by claim 1, wherein the molar ratio of polar aprotic solvent to p-phenol sulfonate ranges from 5 to 50.

9. The process as defined by claim 8, wherein the molar ratio of solvent to p-phenol sulfonate ranges from 5 to 10.

10. The process as defined by claim 9, wherein the molar ratio of solvent to p-phenol sulfonate ranges from 7 to 10.

11. The process as defined by claim 1, wherein the molar ratio of organic sulfonic acid to p-phenol sulfonate is in excess of about 0.01.

12. The process as defined by claim 11, wherein the molar ratio of organic sulfonic acid to p-phenol sulfonate is about 0.02.

13. The process as defined by claim 1, wherein the reaction temperature is in excess of about 100° C.

14. The process as defined by claim 1, further comprising recovering the product para-acyloxybenzene sulfonate from the reaction mixture by washing same with acetone.

15. The process as defined by claim 14, said washing being at a temperature of at least 90° C.

16. The process as defined by claim 14, said washing being with an amount of acetone approximately the same as the amount of solvent present.

17. The process as defined by claim 13, said reaction temperature ranging from 110° to 120° C.

18. The process as defined by claim 1, said acid anhydride comprising heptanoic, octanoic, caprylic, nonanoic, pelargonic, decanoic, capric, dodecanoic or lauric anhydride.

19. The process as defined by claim 1, said acid anhydride comprising pelargonic anhydride or 3,5,5-trimethylhexanoic anhydride.

20. The process as defined by claim 1, said organic sulfonic acid having the general formula (II):

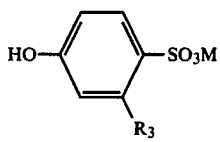
(II)

wherein $R_3$ is hydrogen, an alkyl radical having from 1 to 12 carbon atoms, haloalkyl, phenyl, alkylphenyl, nitro, halogen or —$SO_3M$.

21. A process for the preparation of a paraacyloxybenzene solfonate having the general formula (I):

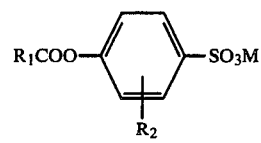

wherein $R_1$ is a straight or branched chain aliphatic radical having from 6 to 11 carbon atoms, $R_2$ is hydrogen, halogen, an alkyl radical having from 1 to 4 carbon atoms, or the radical —$SO_3M$, and M is an alkali metal, which process comprises acylating an alkali metal p-phenol sulfonate with an anhydride of a straight or branched chain carboxylic acid having from 7 to 12 carbon atoms, in a polar aprotic solvent and in the presence of a catalytically effective amount of an organic sulfonic acid.

22. The process as defined by claim 21, said p-phenol sulfonate comprising sodium or potassium p-phenol sulfonate.

23. The process as defined by claim 21, said acid anhydride comprising octanoic, dodecanoic or 3,5,5,-trimethylhexanoic anhydride.

* * * * *